(12) United States Patent
Palti

(10) Patent No.: US 7,228,053 B1
(45) Date of Patent: Jun. 5, 2007

(54) TRANSPORTING MATTER THAT IS ENCLOSED WITHIN A CONTAINER THROUGH A HOLLOW OPTICAL FIBER

(76) Inventor: Yoram Palti, 51 Ruth St., Haifa (IL) 34404

( * ) Notice: Subject to any disclaimer, the term of this patent is extended or adjusted under 35 U.S.C. 154(b) by 134 days.

(21) Appl. No.: 11/157,493

(22) Filed: Jun. 20, 2005

Related U.S. Application Data

(60) Provisional application No. 60/581,502, filed on Jun. 21, 2004.

(51) Int. Cl.
*G02B 6/00* (2006.01)
*G02B 6/032* (2006.01)

(52) U.S. Cl. ...................... 385/147; 385/125

(58) Field of Classification Search .............. 385/125, 385/147
See application file for complete search history.

(56) References Cited

U.S. PATENT DOCUMENTS 6,636,676 B1 * 10/2003 Renn .......................... 385/125
6,823,124 B1 * 11/2004 Renn et al. ................. 385/125
7,045,015 B2 * 5/2006 Renn et al. ................. 118/686

* cited by examiner

*Primary Examiner*—Sarah Song
(74) *Attorney, Agent, or Firm*—Proskauer Rose LLP

(57) ABSTRACT

A payload is enclosed within a container that is dimensioned to fit within the channel that runs through a hollow optical fiber. The container is also adapted to carry a payload. When laser light shines into the optical fiber, some of the laser light strikes the container and propels the container through the channel. As a result, the payload is transported through the hollow fiber.

19 Claims, 5 Drawing Sheets

TRANSPORTING MATTER THAT IS ENCLOSED WITHIN A CONTAINER THROUGH A HOLLOW OPTICAL FIBER

CROSS REFERENCE TO RELATED APPLICATIONS

This application claims priority to U.S. provisional application No. 60/581,502, filed Jun. 21, 2004.

BACKGROUND

Transportation of materials from one location to another requires energy and is usually achieved either by a transporting vehicle or, when the material to be transported is fluid or particulate, by flow. In the first case the movement is done by a device equipped with a motor or other mechanical arrangement that performs work involving such movement. In the second case the movement results directly from forces due to pressure differences, gravitation, etc.

In all such cases the required energy is obtained from various sources such as burning fuel, electric current, etc. In practice, gravitation and similar forces cannot maintain movement continuously and effectively.

A source of energy that has only recently been used to directly create movement, although predicted by Maxwell's theorem, is light. It is now well established that a light beam illuminating a solid surface, preferably of reflective nature, exerts force or pressure on that surface. Such forces are also well known in astronomy. Light force or pressure, has recently been utilized, for example using laser beams, to maneuver micro-organelles and even molecules within cells and often termed optic tweezers.

SUMMARY OF THE INVENTION

The present invention is directed to transporting matter that is enclosed within a container through a hollow core optical fiber.

DESCRIPTION OF THE PREFERRED EMBODIMENTS

FIG. 1 is a schematic representation of an embodiment of the present invention for transporting small quantities of material using light beams. FIG. 1 shows a hollow optic fiber 19 (an optic waveguide). Such fibers have been used to convey visible light, IR, X-Rays, etc. Basically these fibers, which measure a few microns in diameter, can convey light effectively in the hollow part of the fiber 1 by repeated reflections from the fiber walls 2. Such light conduction is similar to the conduction in solid optic fibers that are usually coated by cladding that reflects the light along the fiber. The reflection is due to the difference in the optic properties of the wall and the air or fluid filling the fiber.

Figure 2:
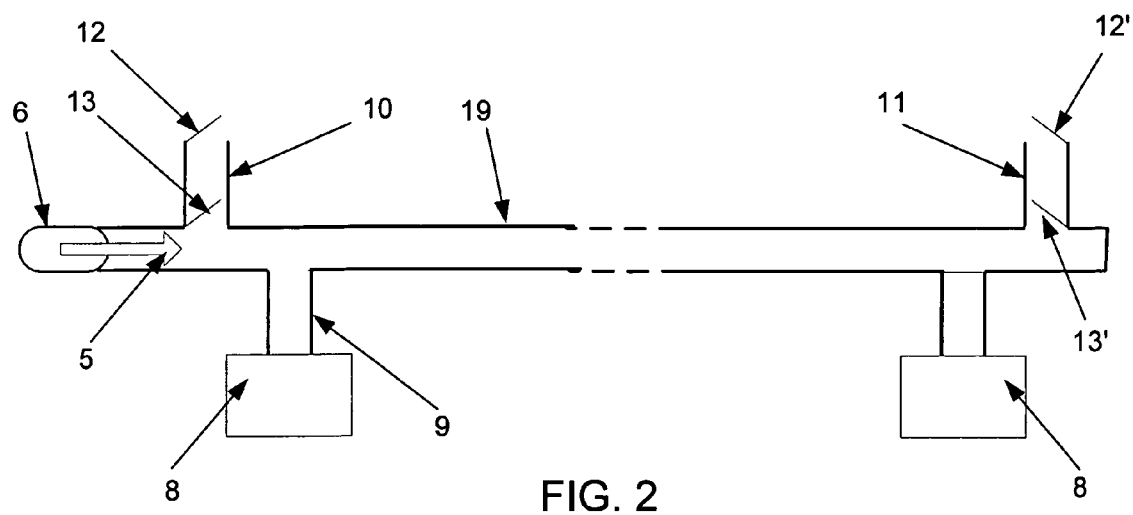
FIG. 2 is an overall schematic diagram of an embodiment of the invention

Turning now to FIG. 2, when a small object that is not transparent at the relevant wavelength resides in the hollow of the fiber, and a light or any other electromagnetic wave beam 5 from a source 6 is directed along the fiber 19, the light exerts force on the object in the direction of the light propagation. The force is directly proportional to the light intensity and inversely related to light velocity. In practice, for visible light and a object with a reflective surface normal to the light beam, the force (F) exerted by a light of 1 Watt intensity is on the order of $3.4 \times 10^{-9}$ Newton. Such a force is sufficient to accelerate the object within the fiber. The magnitude of the acceleration is directly proportional to the light intensity (I), and inversely proportional to the object mass (m), the viscosity (z) of the medium filling the hollow fiber and the friction (r) of the object with the fiber walls.

Optionally, the viscosity experienced by the object as it travels through the core can be lowered by filling the fiber hollow core with gas, preferably under very low pressure. This may be done using a vacuum pump 8 connected to the fiber 19 through port 9. To maintain the low pressure in the fiber hollow core, the objects to be transported are introduced into and taken out off the fiber hollow core through appropriately seal maintaining ports 10 and 11 respectively. This is done, for example, by ports equipped with double doors (12, 13 at the input end and 12', 13' at the output end) arranged such that one door leading to the core is always closed. The energy of a laser with an output in the 1 mW–10 W range is sufficient to rapidly (seconds to minutes travel time for distances in the order of a mile) transport masses in the order of nanograms to milligrams, depending on the specific conditions. For example, a 1 Watt light would cause an object weighting 1 nanogram to accelerate at over 100 $m/S^2$.

Figure 1A:
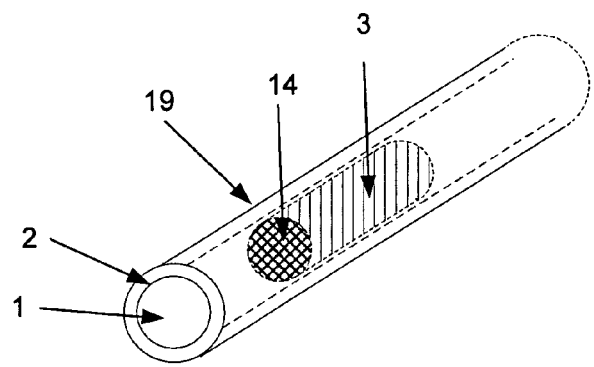
FIG. 1A shows a hollow core optical fiber with a cylindrical container positioned within the core.

The objects to be transported through the hollow fiber core by the force or pressure exerted by light must either absorb the light or have a reflecting surface set at an angle approximately normal to the beam direction. An example of such a object is shown in FIG. 1A, where the object 3 has a cylindrical shape positioned with its long axis along the fiber axis and having a flat reflective surface 14 facing the beam (i.e., normal to beam axis).

Figure 1B:
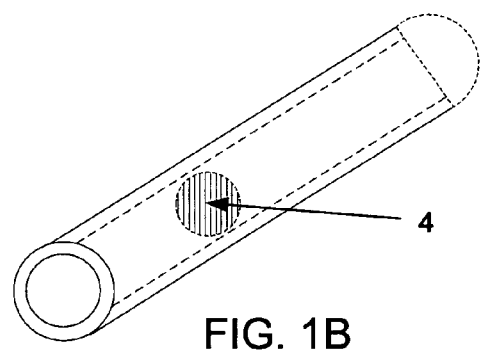
FIG. 1B shows a hollow core optical fiber with a spherical container positioned within the core.

It is also possible to implement light-propelled motion using a non-flat surface, such as the curved surface of a spherical container 4 shown in FIG. 1B, or a surface that is not exactly positioned at the right angle. Although these shapes will be less effective because they will lose a corresponding fraction of the effective push power, this loss can be compensated for by using a more intense light beam. The reflective surface may be made for example from a thin gold leaflet or plating. The force pushing an object with a perfect reflector may be as much as twice as strong as that pushing an object that fully absorbs the light energy.

The transported object preferably serves as a container vehicle for carrying a payload material. Within this framework the containers size and shape can be optimized for the transport for a specific set of hollow fibers. For example, consider two general shapes: cylindrical and spherical, as depicted in FIGS. 1A and 1B. When a cylindrical container is used, the diameter of the cylinder is preferably smaller than the internal diameter of the hollow core such that it will move freely but not wobble or turn over. For example, if the internal diameter of the fiber is 100 μm, a suitable size for the container would be between 10 and 50 μm in diameter. Similarly, if the internal diameter of the fiber is 50 μm, a suitable size for the container would be between 5 and 25 μm in diameter. As described above, the surface facing the light source is preferably flat and a light reflector at the relevant wavelength. The cylinder is preferably formed of a material with appropriate mechanical and optical properties to carry the payload to its destination. Examples of suitable materials include plastics (e.g., polyethylene, polycarbonate, Lucite, polyurethane, etc.), light weight metal alloys (e.g., magnesium, titanium, etc.), and Carbon tubes of small diameter ("nano-tubules").

Figure 3:
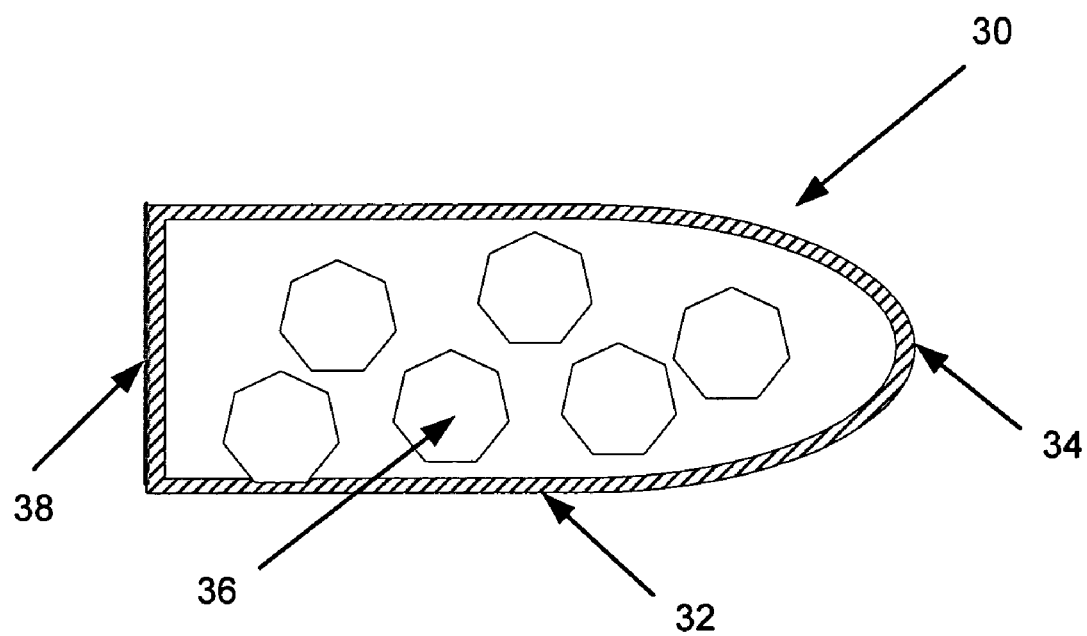
FIG. 3 is a cutaway view of a bullet-shaped container.

FIG. 3 is a cutaway view of a bullet-shaped object that is used as a container 30 for transporting the payload 37 through the fiber. The wall 32 of the container 30 has a shape and mechanical properties that permit it to slide through the fiber as described above, and also permit it to contain the payload 36. Optionally, the front 34 of the container 30 may be rounded to reduce aerodynamic drag. Preferably, the rear 38 of the container 30 is flat, and it reflects the light beam that arrives from the left.

Figure 4:
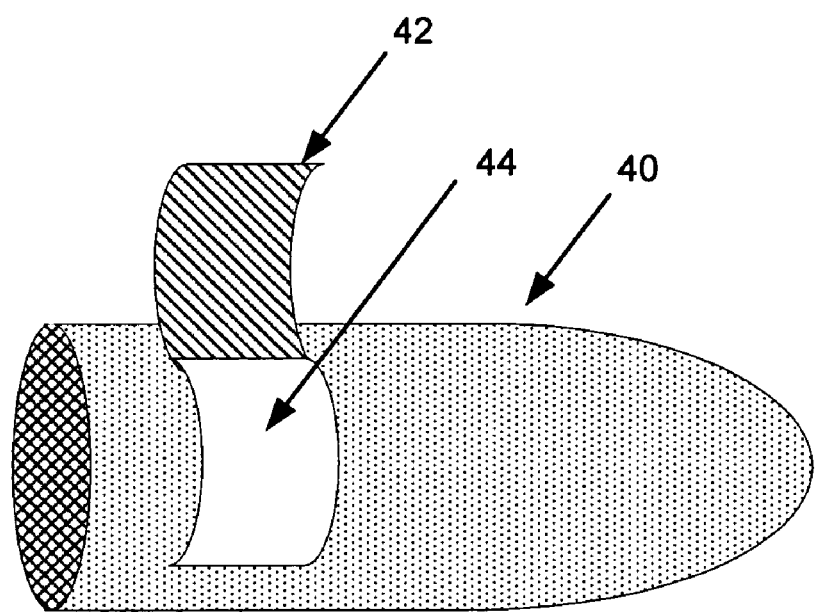
FIG. 4 is an external view of a bullet-shaped container with a door for loading material into the container.

FIG. 4 is an external view of a bullet-shaped material container 40 with a door 42 for loading payload the material into the carrier. When the door 42 is opened, there is an opening 44 through which a payload material 36 (shown in FIG. 3) may be introduced. When the door is closed, the payload is completely enclosed within the container 40. The container may be manufactured using techniques such as injection molding, micro-machining, vacuum forming, extrusion, etc., which are well known to persons skilled in the relevant arts.

Figure 5:
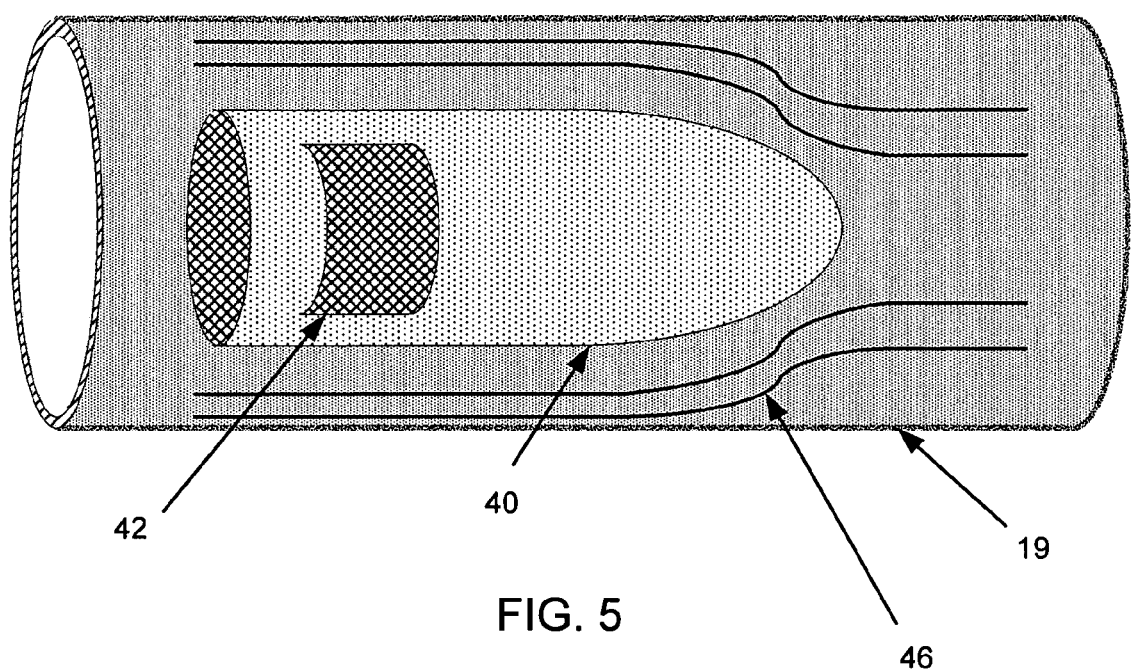
FIG. 5 depicts the bullet-shaped container of FIG. 4 positioned within the hollow optical fiber.

FIG. 5 depicts a bullet shaped material container 40 with its door 42 in the closed position. As the container 40 travels through a hollow optic fiber 19, there is space above, below, and on all sides of the container 40, which permits the container to travel through the fiber 19 freely. Flow lines 46 depict the lines of air flow that surround the container which keep the container spaced away from the wall. To maintain such spacing, the diameter of the container is preferably between one-tenth and one-half the size of the inner diameter of the hollow fiber 19.

Figure 6A:
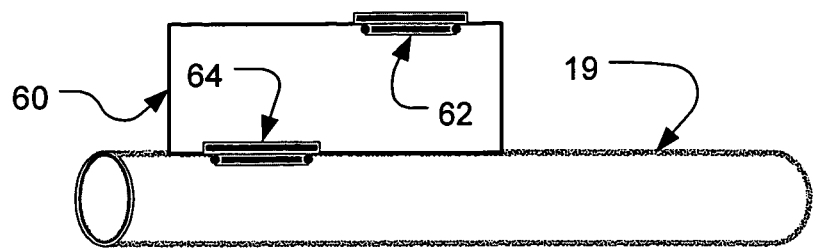
FIGS. 6A–6D depict an air lock for maintaining a vacuum inside the hollow fiber.
Figure 6B:
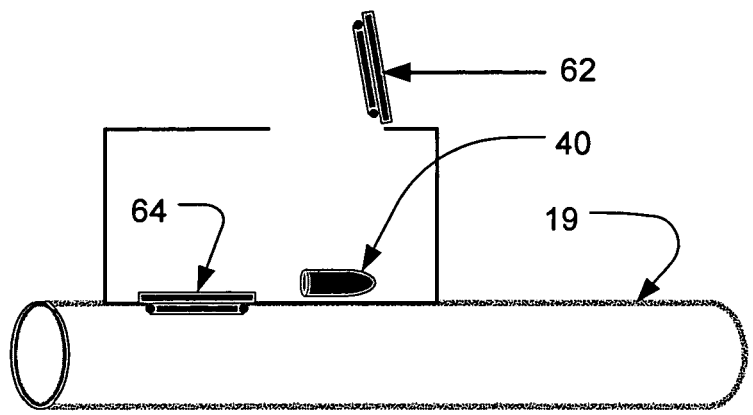
Figure 6C:
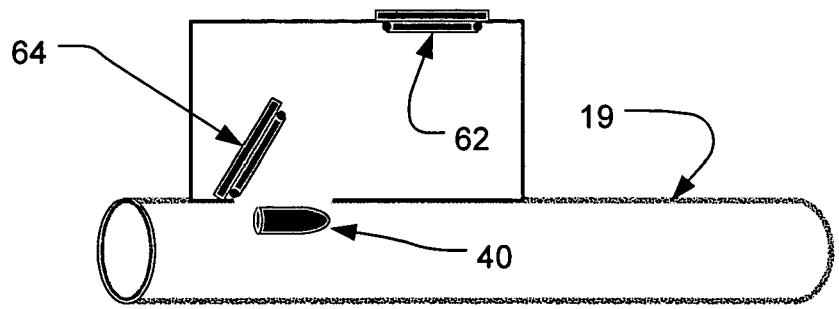
Figure 6D:
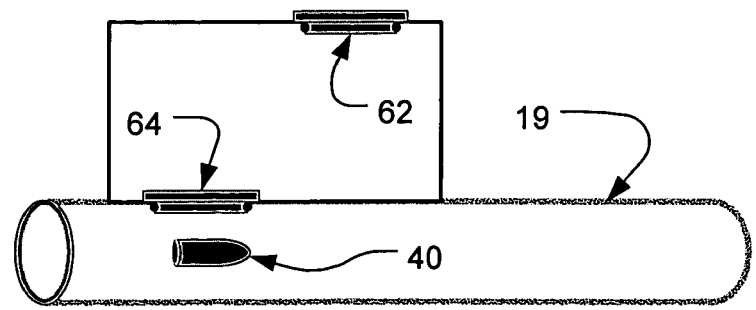

FIGS. 6A–6D depict an airlock for maintaining a vacuum inside the hollow fiber. Preferably, the vacuum is maintained so that the air pressure within the hollow optic fiber 19 is less than about 0.1 atm. This may be accomplished using a two port airlock 60 that is connected to the hollow optic fiber 19. The airlock 60 contains two sealing caps 62, 64. Ordinarily, both of these caps 62, 64 are closed, as seen in FIG. 6A. To position a container into the hollow optic fiber for transport through the fiber, first the upper cap 62 is opened, and the container 40 is inserted into the airlock as seen in FIG. 6B. Subsequently, the upper cap 62 is closed and the lower cap 64 is opened, and the container 40 is moved into the hollow optic fiber 19, as seen in FIG. 6C. After the container 40 is positioned within the fiber 19, the lower cap 64 is closed, as seen in FIG. 6D, after which the laser is activated to propel the container 40 through the fiber 19. Movement of the containers through the airlock may be accomplished, for example, by using a 2D or 3D micromanipulator or a robotic arm.

Figure 7:
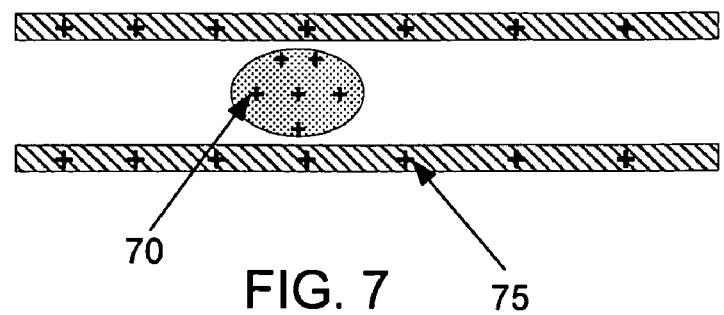
FIG. 7 shows how charge can be used to reduce contact with the inner walls of the fiber.

The outer surface of the container is preferably smooth and may optionally be made of a material that has minimal friction with the fiber walls, such as Teflon. Optionally, a friction lowering lubricant can also be used. An additional way to lower the force required to move the container is to eliminate contact with the walls so as to eliminate or greatly reduce friction. This can be done, for example, by magnetic or electrostatic forces. Most dielectrics carry a net electrostatic charge. The charge can be increased or generated, for example, by making contact with a charged body, or by friction with an appropriate material (like charging a comb by friction with hair or wool). The friction can be achieved by moving, from time to time, an appropriate container in the fiber or externally around the fiber or a whole bunch of fibers. In such a case, the container will carry the same charge as the fiber wall. For example, as shown in FIG. 7, both the object 70 and the fiber walls 75 have a positive charge so that the object 70 will be repelled from the walls 75 of the hollow fiber core. The container can be permanently charged, or charged before entering the fiber.

Similar considerations hold for a ball-like container, which advantageously has significantly lower friction with the walls. The diameter of the spherical container is preferably between one-tenth and one-half the size of the inner diameter of the hollow fiber 19. At low pressures (e.g., less than about 0.1 atm), the diameters of the sphere can be increase up to 80% or even 90% of the inner diameter of the fiber.

Figure 8A:
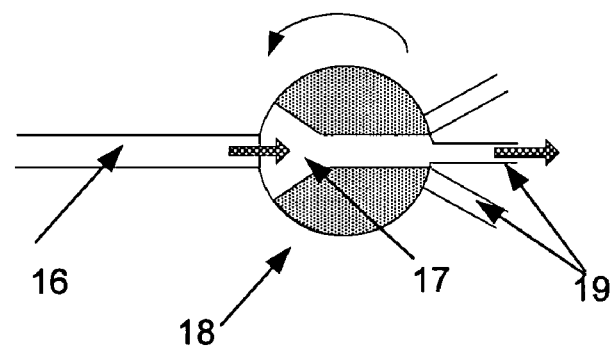
FIGS. 8A and 8B show a routing system for routing a container along a desired path.
Figure 8B:
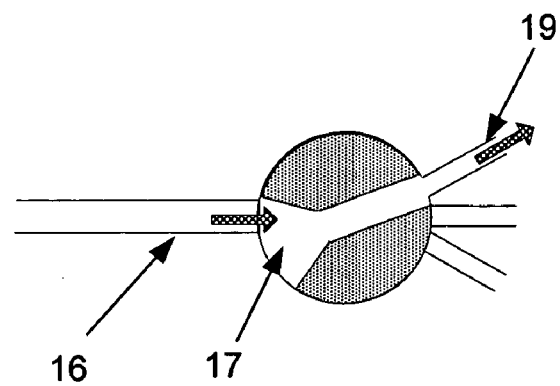

In some embodiments, the hollow fibers are continuous from the origin to the final destination. In alternative embodiments, route selectors analogous to those used in communications systems can be used. FIGS. 8A and 8B illustrate a suitable selector 18 that accepts light from an incoming fiber 16 into an interim chamber 17, the output of which can be directed, as desired, into the specific hollow output fiber 19 leading to the required destination. In practice, the selector switch can connect one of many inputs to one of many outputs under computer control. Movement through the small distances associated with such selectors can be implemented using light force or mechanical forces such as pressure differences.

The described system for transportation of materials from one location to another may have significant advantages in many cases. Some examples are:

Currently, telemedicine is mainly used to transmit medical information from one location to another; clinic to clinic, or patient home to clinic. The material transportation system of the invention can be extremely useful in enabling the transport of blood samples, urine samples, throat swab, cell and tissue samples, etc., from one medical facility or portion of a medical facility to another, or from the patient's home to a medical facility. Small therapeutic agents can be sent in the reverse direction. In general the fibers can be used for two-way communication.

Transport of air, water, dust or any contamination samples from the "field", airport checkpoints, etc. to central analysis and interpretation units.

Adding odorants, etc. to cable TV viewers etc. The images and the materials can use the same optic fibers, or separate ones.

The following references are indicative of the state of the art, and are hereby incorporated herein by reference: U.S. Pat. Nos. 4,893,886, 4,327,288, and 6,636,676; S. Block, "Making light work with optical tweezers" Nature 360 (6403): 493–5 (1972); K. Avoboda and S. Block, "Biological forces of optical forces" Annu Rev Biophys Biomol Struct 23:247–85 (1994); R. Simmons et al., "Quantitative measurements of force and displacement using an optical trap" Biophys. J 70: 1813–22 (1996); A. Ashkin, "History of optical trapping and manipulation of small-neutral particles, atoms and molecules" IEEE Journal of Selected Topics in Quantum Electronics 6:841–856 (2000); Lang, et al., "An automated two-dimensional optical force clamp for single molecule studies." Biophys. J 83:491–501 (2002); Y. Matsuura et al., "Optical properties of small-bore hollow glass waveguides," Applied Optics, 34, 6842–6847, (1995); R. Kozodoy et al., "Small-bore hollow waveguides for delivery of 3 micron laser radiation," Applied Optics, 35, 1077–1082, (1996); J. Harrington et al., "Transmission properties of hollow glass waveguides for the delivery of CO2 surgical laser power," IEEE Journal of Selected Topics in Quantum Electronics, 5, 948–953 (1999).

I claim:

1. An apparatus comprising:
   a hollow-core optical fiber having an inner surface, wherein the inner surface circumscribes a channel within the optical fiber;
   a non-liquid container that is dimensioned to fit within the channel, wherein the container is adapted to carry a payload; and
   a laser configured to shine laser light into optical fiber so that when the container is located within the channel, at least some of the laser light strikes the container and propels the container through at least a portion of the channel.

2. The apparatus of claim 1, wherein a vacuum is maintained within the channel.

3. The apparatus of claim 1, wherein the container is configured to completely enclose the payload while the container is being propelled.

4. The apparatus of claim 3, wherein the container has a sealable opening through which the payload can be inserted.

5. The apparatus of claim 1, wherein the container is configured so that the laser light that strikes the container strikes a reflective surface of the container.

6. The apparatus of claim 1, wherein a ratio of the outer diameter of the container to the diameter of the channel is between 0.1 and 0.5.

7. The apparatus of claim 1, wherein the container is configured to completely enclose the payload while the container is being propelled, wherein the container is configured so that the laser light that strikes the container strikes a reflective surface of the container, and wherein a ratio of the outer diameter of the container to the diameter of the channel is between 0.1 and 0.5.

8. A method of propelling a payload through a hollow-core optical fiber, the method comprising the steps of:
   loading the payload into a non-liquid container that is dimensioned to fit within the hollow core of the optical fiber;
   loading the container into the hollow core of the optical fiber; and
   shining laser light into the optical fiber so that at least some of the laser light strikes the container and propels the container through at least a portion of the hollow core of the optical fiber.

9. The method of claim 8, further comprising the step of maintaining a vacuum is within the hollow core of the optical fiber.

10. The method of claim 8, wherein the container is configured to completely enclose the payload while the container is being propelled though the hollow core of the optical fiber.

11. The method of claim 10, wherein the container has a sealable opening through which the payload is loaded.

12. The method of claim 8, wherein the container is configured so that the laser light that strikes the container strikes a reflective surface of the container.

13. The method of claim 8, wherein a ratio of the outer diameter of the container to the diameter of the hollow core of the optical fiber is between 0.1 and 0.5.

14. A method of propelling a payload through a hollow-core optical fiber, the method comprising the steps of:
   positioning a non-liquid container that contains the payload into the hollow core of the optical fiber; and
   shining laser light into the optical fiber so that at least some of the laser light strikes the container and propels the container through at least a portion of the hollow core of the optical fiber.

15. The method of claim 14, further comprising the step of maintaining a vacuum is within the hollow core of the optical fiber.

16. The method of claim 14, wherein the container is configured to completely enclose the payload while the container is being propelled.

17. The method of claim 16, wherein the container has a sealable opening through which the payload is loaded.

18. The method of claim 14, wherein the container is configured so that the laser light that strikes the container strikes a reflective surface of the container.

19. The method of claim 14, wherein a ratio of the outer diameter of the container to the diameter of the hollow core of the optical fiber is between 0.1 and 0.5.

* * * * *